US00PP19370P2

(12) United States Plant Patent
Izumi

(10) Patent No.: US PP19,370 P2
(45) Date of Patent: Oct. 21, 2008

(54) ***SALIX* PLANT NAMED 'GOLDEN SUNSHINE'**

(50) Latin Name: *Salix sachalinensis*
Varietal Denomination: Golden Sunshine

(76) Inventor: Takuya Izumi, 799-3104, Ehime, Iyo-city, 1606-4 Kamimitani (JP)

( * ) Notice: Subject to any disclaimer, the term of this patent is extended or adjusted under 35 U.S.C. 154(b) by 0 days.

(21) Appl. No.: 11/879,175

(22) Filed: Jul. 16, 2007

(51) Int. Cl.
*A01H 5/00* (2006.01)

(52) U.S. Cl. ..... Plt./216

(58) Field of Classification Search ..... Plt./216, Plt./226

See application file for complete search history.

*Primary Examiner*—Kent L. Bell
(74) *Attorney, Agent, or Firm*—Audrey Charles

(57) ABSTRACT

A new and distinct cultivar of *Salix* plant named 'golden Sunshine', characterized by its golden-colored spring foliage that matures to chartreuse-colored autumn foliage, and compact growth habit.

1 Drawing Sheet

Latin name of genus and species of plant claimed: *Salix sachaliensis.*
Variety denomination: 'Golden Sunshine'.

BACKGROUND OF THE INVENTION

The present invention relates to a new and distinct cultivar of *Salix* plant botanically known as *Salix sachalinensis* and hereinafter referred to by the cultivar name 'Golden Sunshine'.

The new *Salix* cultivar is a naturally-occurring whole plant mutation discovered in a controlled planting of the species *Salix sachalinensis,* not patented. The species *Salix sachalinensis* is characterized by its green-colored foliage and large rounded growth habit. The species *Salix sachalinensis* is a small tree growing to 6 m (20 feet) high, typically as a multi-trunk with a spreading growth habit. The plant is native to Japan including Shikoku, Honshu, and Hokkaido.

The new cultivar was discovered and selected as a single plant within a population of plants of *Salix sachalinensis* during January 2005 in a controlled environment at Iyo-city, Japan.

Asexual reproduction of the new cultivar by terminal stem cuttings since August 2005 at Iyo-city, Japan has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Golden Sunshine' as a new and distinct cultivar of *Salix* plant:

1. Golden-colored spring foliage that matures to chartreuse-colored autumn foliage; and
2. Compact growth habit.

Plants of the new cultivar differ from plants of the parent *Salix sachalinensis* species in foliage color and growth habit.

The only commercially available *Salix sachalinensis* cultivar known to the inventor, is the cultivar 'Sekka', not patented. Plants of the new cultivar differ from plants of 'Sekka' primarily in branch orientation as plants of 'Sekka' typically have twisted and contorted branches.

Plants of the parent species *Salix sachalinensis* are the most similar in comparison to the new cultivar. However, in comparison, plants of the new cultivar differ from plants of *Salix sachalinensis* in the following characteristics:

1. Plants of the new cultivar have a golden-colored spring foliage that matures to chartreuse-colored autumn foliage, while plants of the species have green foliage; and
2. Plants of the new cultivar exhibit compact growth habit as compared to the species.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Golden Sunshine'. The plant illustrated was grown for approximately two years in an outdoor nursery in Iyo-city, Japan.

DETAILED BOTANICAL DESCRIPTION

Figure 1:
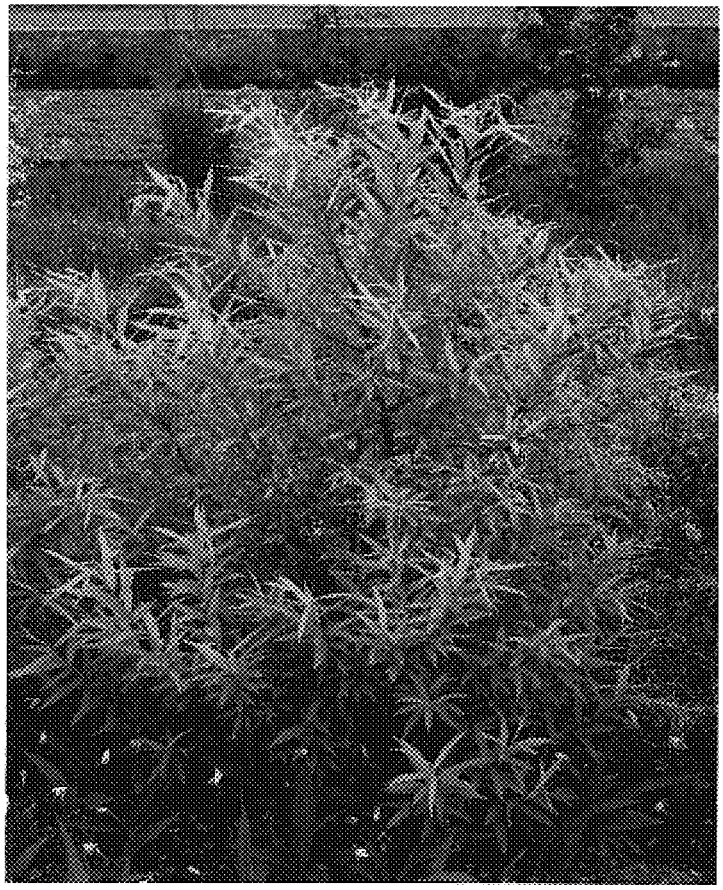
FIG. 1 illustrates the overall growth and habit of 'Golden Sunshine'.
Figure 2:
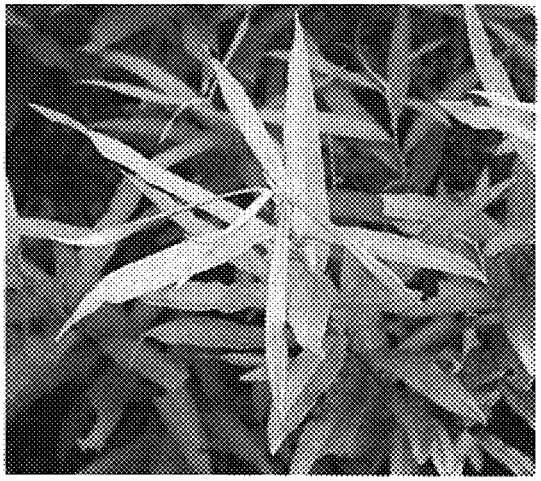
FIG. 2 illustrates a close-up view of the foliage of 'Golden Sunshine'.
Figure 3:
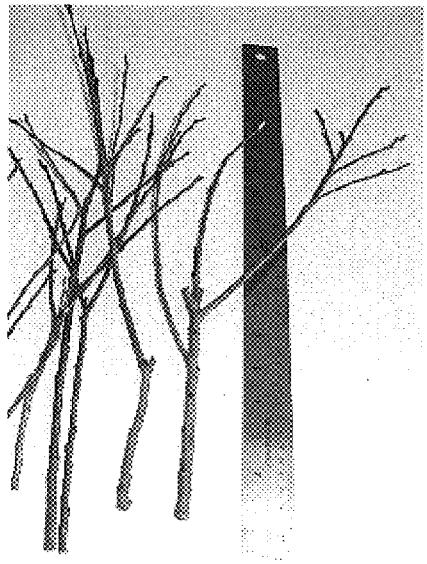
FIG. 3 illustrates a close-up view of stem cuttings of 'Golden Sunshine'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined under natural light conditions in Iyo-city, Japan.

The following descriptions and measurements describe plants produced from cuttings and grown in a cultivated area of an outdoor nursery in Iyo-city Japan. The plant size and description are based on plants grown for approximately two years with day temperatures ranging from 8° C. to 31° C. (47° F. to 87° F.) and night temperatures ranging from 1° C. to 24° C. (34° F. to 75° F.)

Botanical classification: *Salix sachalinensis* cultivar Golden Sunshine.

Parentage:

*Parents.*—*Salix sachalinensis* F. Schmidt, (S. opaca Seem.).

General plant description:

*Overall habit.*—'Golden Sunshine' is a compact growing deciduous shrub or small tree. Mature specimen is 4 meters tall and 3 meters wide. Branching typically multi-stem arising from several trunks located close to the ground. Lateral branches are numerous and sparsely pubescent becoming glabrous, glossy as they mature.

*Overall size.*—Height varies dependent upon climatic exposure and soil. A plant in the landscape, in full sun measures about 4 meters tall and 3 meters wide.

Propagation:

*Type cutting.*—Hardwood.

*Time to initiate roots.*—Approximately 3 to 5 days.

*Time to produce a rooted cutting.*—Approximately 10 to 15 days.

*Root description.*—Fibrous, hairy.

*Rooting habit.*—Freely branching.

Plant description:

*Commercial crop time.*—Approximately 6 to 8 weeks from a rooted cutting to finish in an approximately 5 cm pot.

*Size.*—Height from soil level to top of plant plane: Approximately 4 m. Width: Approximately 3 m.

*Branching habit.*—Freely branching. Quantity of main branches per plant: Approximately 8.

*Branch.*—Strength: Strong, becomes woody with age. Length: Approximately 51.3 cm. Diameter: Approximately 2.3 cm. Length of central internode: Approximately 2.3 cm. Texture: Sparsely pubescent, becoming glabrous with age. Color of developing stems: N170B. Color of fully developed stems: 191B.

Foliage description:

*General description.*—Quantity of leaves per main branch: Ranges from 250 to 1000. Fragrance: None observed. Form: Simple. Arrangement: Alternate.

*Leaves.*—Aspect: Obtuse angle to stem. Shape: Lanceolate. Margin: Entire. Apex: Acuminate. Base: Cuneate. Venation pattern: Pinnate. Length of mature leaf: Approximately 8.3 cm. Width of mature leaf: Approximately 1.7 cm. Texture of upper and lower surfaces: Silky pubescence when young, becoming glabrous with age. Color of upper surface of young foliage: 150B with venation of 150B and midvein at base of 178B transitioning to 150B toward apex. Color of lower surface of young foliage: 152D with venation of 152D. Color of upper surface of mature foliage: N144B with venation of N144B. Color of lower surface of mature foliage: 144B with venation of 144B.

*Petiole.*—Length: Approximately 5.0 mm. Diameter: Approximately 1.0 mm. Texture: Glabrous. Color: 150B.

*Stipule.*—Length: Approximately 3.0 mm Width: Approximately 2.0 mm. Texture: Glabrous. Color: 150B.

Flowering description: No flowers have been observed.

Disease and pest resistance: Resistance to pathogens and pests common to *Salix* has not been observed.

What is claimed is:

1. A new and distinct cultivar of *Salix* plant named 'Golden Sunshine', substantially as herein shown and described.

* * * * *